(12) United States Patent
Harada (10) Patent No.: US 12,383,121 B2
(45) Date of Patent: Aug. 12, 2025

(54) DISTAL-END-CAP DETACHMENT JIG

(71) Applicant: FUJIFILM Corporation, Tokyo (JP)

(72) Inventor: Takashi Harada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 167 days.

(21) Appl. No.: 17/374,190

(22) Filed: Jul. 13, 2021

(65) Prior Publication Data
US 2022/0061637 A1    Mar. 3, 2022

(30) Foreign Application Priority Data
Aug. 26, 2020  (JP) ................. 2020-142536

(51) Int. Cl.
*A61B 1/00* (2006.01)
*A61B 1/018* (2006.01)

(52) U.S. Cl.
CPC ...... *A61B 1/00101* (2013.01); *A61B 1/00098* (2013.01); *A61B 1/00137* (2013.01); *A61B 1/018* (2013.01)

(58) Field of Classification Search
CPC ............ A61B 1/00101; A61B 1/00098; A61B 1/00137; A61B 1/018; A61B 1/0008; A61B 1/00128; A61B 1/0676; A61M 5/3204
See application file for complete search history.

(56) References Cited

U.S. PATENT DOCUMENTS

| | | | | |
|---|---|---|---|---|
| 5,707,344 A | * | 1/1998 | Nakazawa | A61B 1/00098 600/125 |
| 11,096,558 B2 | * | 8/2021 | Yamaya | G02B 23/26 |
| 11,272,832 B2 | * | 3/2022 | Yamaya | A61B 1/0014 |
| 11,330,967 B2 | * | 5/2022 | Yamaya | A61B 1/00137 |
| 2018/0317741 A1 | | 11/2018 | Yamaya | |
| 2019/0142242 A1 | | 5/2019 | Yamaya | |

FOREIGN PATENT DOCUMENTS

| | | | |
|---|---|---|---|
| JP | 7-184838 A | 7/1995 | |
| JP | 9-75295 A | 3/1997 | |
| WO | WO 2017/122692 A1 | 7/2017 | |
| WO | WO 2018/051626 A1 | 3/2018 | |
| WO | WO-2018190225 A1 * | 10/2018 | ......... A61B 1/00089 |

OTHER PUBLICATIONS

Office Action issued in counterpart Japanese Application No. 2020-142536 on Mar. 2, 2023, with English translation.

* cited by examiner

*Primary Examiner* — Michael J Carey
*Assistant Examiner* — Megan Elizabeth Monahan
(74) *Attorney, Agent, or Firm* — Birch, Stewart, Kolasch & Birch, LLP (57) ABSTRACT

Provided is a distal-end-cap detachment jig capable of safely detaching a distal end cap from a distal-end-portion body. A distal-end-cap detachment jig that is used to detach a distal end cap mounted on a distal end of a side-viewing scope and having an inner space which communicates with a cap opening allowing a passage of a treatment tool, includes at least a body portion that has an inclined surface, in which the inclined surface is tapered in a direction of insertion into the inner space of the distal end cap, and in a case where the body portion is inserted into the inner space of the distal end cap, the inclined surface deforms the distal end cap in a direction of expanding the inner space of the distal end cap.

7 Claims, 10 Drawing Sheets

DISTAL-END-CAP DETACHMENT JIG

CROSS-REFERENCE TO RELATED APPLICATION

The present application claims priority under 35 U.S.C § 119(a) to Japanese Patent Application No. 2020-142536 filed on Aug. 26, 2020, which is hereby expressly incorporated by reference, in its entirety, into the present application.

BACKGROUND OF THE INVENTION

1. Field of the Invention

The present invention relates to a distal-end-cap detachment jig.

2. Description of the Related Art

In the endoscope, various treatment tools are introduced from the treatment tool inlet port provided in the operation part, and the treatment tools are led out of the treatment tool outlet port opened to the distal end of the insertion part to be used for treatment. For example, a treatment tool such as a guide wire or a contrast tube is used in a duodenal endoscope. A treatment tool such as a puncture needle is used in ultrasonic endoscope. A treatment tool such as forceps or a snare is used in other forward-viewing endoscopes and oblique-viewing endoscopes. In order to perform treatment at a desired position in an object to be examined, the lead-out direction of such a treatment tool needs to be changed at a distal end thereof. For this purpose, a distal-end-portion body of the distal end portion is provided with an elevator that changes the lead-out direction of the treatment tool. The endoscope is provided with a treatment-tool elevating mechanism that changes the posture of the elevator between an elevating position and a lying position.

The endoscope needs to be washed after the treatment. JP1995-184838 (JP-H07-184838), JP1997-075295 (JP-H09-075295), WO2017/122692A, and WO2018/051626A disclose that a distal end cap is attachably and detachably mounted on the distal-end-portion body provided with the elevator, and the distal end cap is detached through a jig after the treatment, in order to improve washability.

SUMMARY OF THE INVENTION

Incidentally, there is a concern that the endoscope may be damaged or a load may be applied to the endoscope when the distal end cap mounted on the distal-end-portion body is detached by the jig.

The present invention has been made in view of such circumstances, and an object thereof is to provide a distal-end-cap detachment jig capable of safely detaching the distal end cap from the distal-end-portion body.

A distal-end-cap detachment jig according to a first aspect that is used to detach a distal end cap mounted on a distal end of a side-viewing scope and having an inner space which communicates with a cap opening allowing a passage of a treatment tool, the distal-end-cap detachment jig comprises at least a body portion that has an inclined surface, in which the inclined surface is tapered in a direction of insertion into the inner space of the distal end cap, and in a case where the body portion is inserted into the inner space of the distal end cap, the inclined surface deforms the distal end cap in a direction of expanding the inner space of the distal end cap.

The distal-end-cap detachment jig according to a second aspect, further comprises a connection portion that is connected to the body portion, in which the connection portion is connected at a position opposite to the direction of insertion of the body portion and is provided with a finger hole extending in a direction orthogonal to the direction of insertion.

In the distal-end-cap detachment jig according to a third aspect, the finger hole is a through-hole that penetrates the connection portion.

The distal-end-cap detachment jig according to a fourth aspect, further comprises a connection portion that is connected to the body portion, in which the connection portion includes a fixed arm and a sliding arm that is connected to one end of the fixed arm through a fulcrum portion, the body portion is connected to an end part of the sliding arm on a side opposite to the fulcrum portion, and the body portion can be inserted into the inner space of the distal end cap with the fulcrum portion as a fulcrum.

In the distal-end-cap detachment jig according to a fifth aspect, a side of the fixed arm opposite to the fulcrum portion is formed by a curved surface that follows a shape of the distal end cap.

The distal-end-cap detachment jig according to a sixth aspect, further comprises a connection portion that is connected to the body portion, in which the connection portion has a housing member in which a space that houses the distal end cap is formed, the housing member has a first opening that allows housing the distal end cap and a bottom that faces the first opening, and the body portion is connected to the bottom at a position opposite to the direction of insertion of the body portion.

In the distal-end-cap detachment jig according to a seventh aspect, the space includes an escape space that houses the distal end cap deformed by the body portion.

In the distal-end-cap detachment jig according to an eighth aspect, the housing member has a gutter shape having a second opening that faces a side orthogonal to the direction of insertion of the body portion.

With the distal-end-cap detachment jig according to the aspects of the present invention, it is possible to suppress the damage or load applied to the endoscope.

DESCRIPTION OF THE PREFERRED EMBODIMENTS

Figure 1:
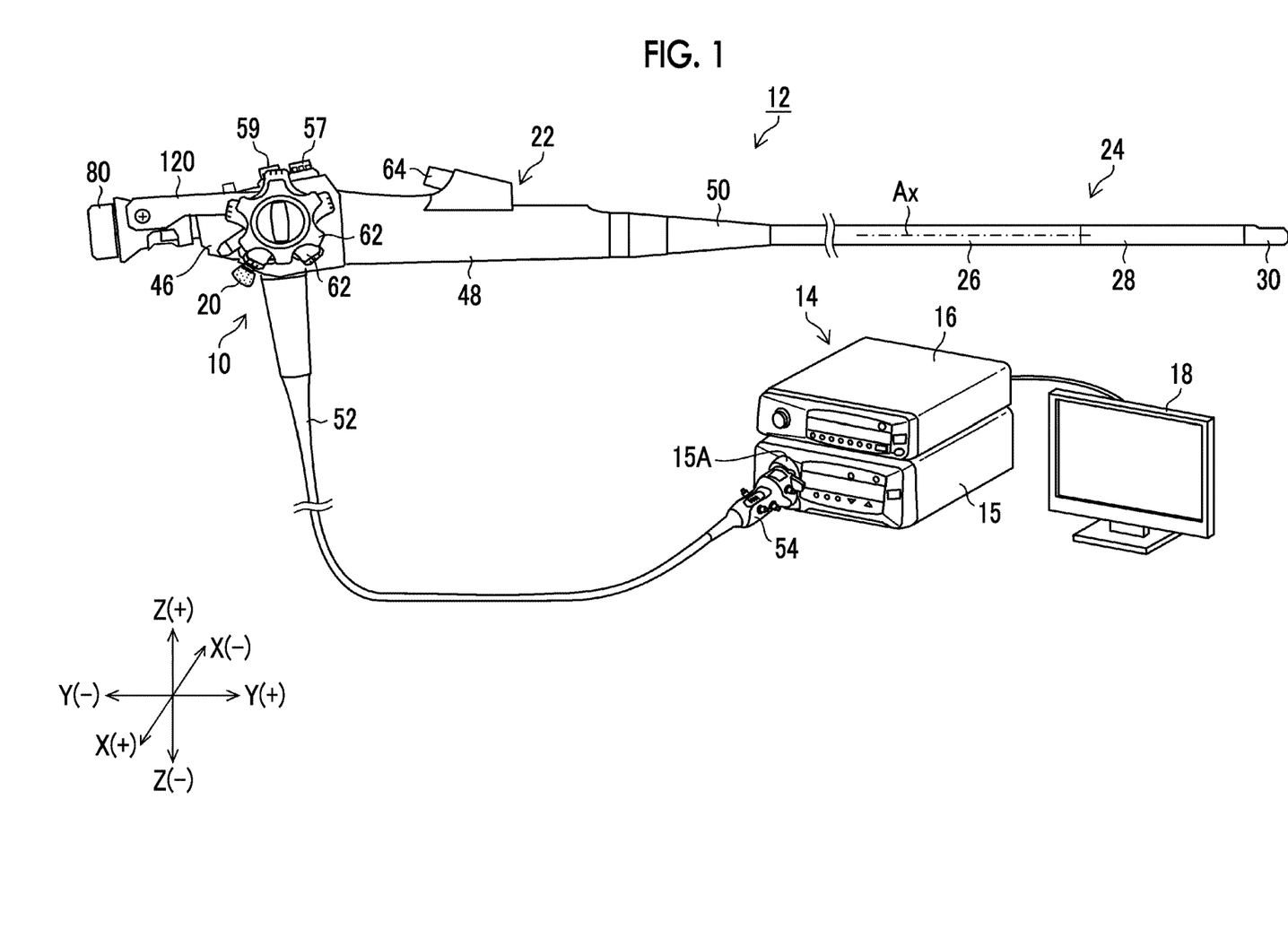
FIG. 1 is a diagram showing a configuration of an endoscope system including an endoscope.

FIG. 1 is a diagram showing a configuration of an endoscope system 12 including an endoscope 10. The endoscope system 12 comprises the endoscope 10, an endoscope processor apparatus 14, and a display 18.

The endoscope 10 comprises a proximal operation part 22 (also referred to as an operation part) provided with an elevating operation lever 20, and an insertion part 24 of which the proximal end is connected to the proximal operation part 22 and which is inserted into an object to be examined. The elevating operation lever 20 is an example of an operation member.

The insertion part 24 has a major axis direction Ax from the proximal end to the distal end, and comprises a soft portion 26, a bendable portion 28, and a distal end portion 30 in this order from the proximal end side to the distal end side. The schematic configuration of the distal end portion 30 will be described.

Figure 2:
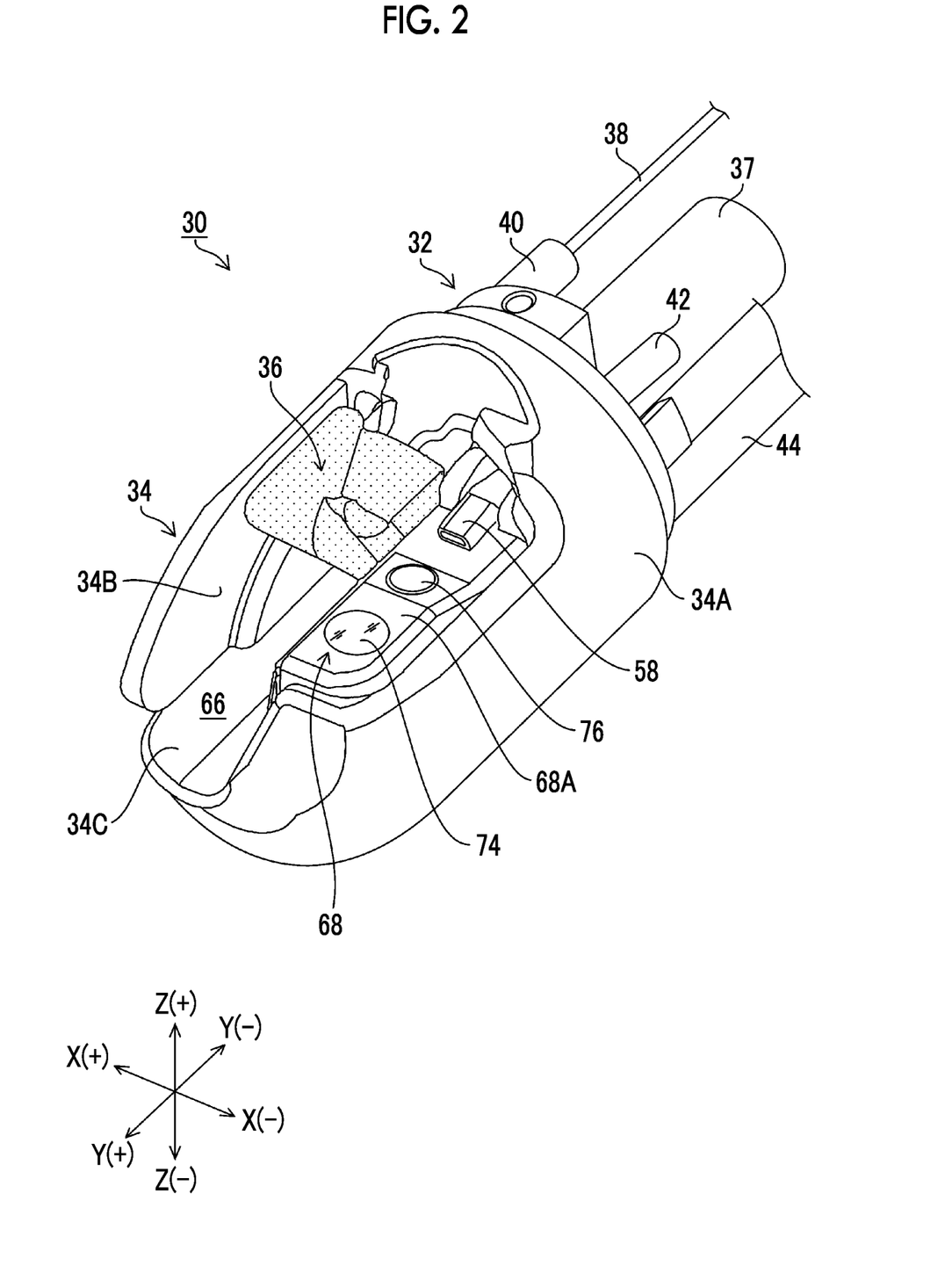
FIG. 2 is a perspective view of a distal end portion.

FIG. 2 is an enlarged perspective view of the distal end portion 30. Here, the endoscope 10 (see FIG. 1) is a side-viewing endoscope (also referred to as a side-viewing scope) that is used as, for example, a duodenal endoscope, and the distal end portion 30 of FIG. 2 has a configuration of a side-viewing endoscope.

In FIG. 2, a distal end cap 34 is mounted on the distal-end-portion body 32, whereby the distal end portion 30 is formed. A treatment tool elevator 36 (hereinafter, elevator 36) is attached to the distal end cap 34.

FIG. 2 shows various components provided in the insertion part 24 of the endoscope 10 (see FIG. 1), in addition to the distal end portion 30. A treatment tool channel 37 that guides the distal end of a treatment tool (not shown) to the distal-end-portion body 32, an elevating operation wire 38 (hereinafter, referred to as a wire 38) that is used to perform operation for changing the lead-out direction of the distal end of the treatment tool led out of the distal-end-portion body 32, a wire channel 40 through which the wire 38 is inserted, an air/water supply tube 42, and a cable insertion channel 44 are shown. An air/water supply nozzle 58 is connected to the air/water supply tube 42 and communicates with the air/water supply tube 42. Further, components such as a light guide (not shown) that guides illumination light supplied from a light source device 15 (see FIG. 1) to the distal-end-portion body 32 and an angle wire (not shown) that is used to perform operation for bending the bendable portion 28 (see FIG. 1) are provided in the insertion part 24. The wire 38 is inserted through the wire channel 40 and disposed therein so as to be able to advance and retreat. The wire channel 40 is disposed from the proximal operation part 22 (see FIG. 1) to the insertion part 24. An illumination window 74 that is used to emit light and an observation window 76 that is used to capture an observation image are provided on the front end face of the distal end portion 30.

In the present specification, a three-dimensional Cartesian coordinate system including three-axis directions (an X-axis direction, a Y-axis direction, and a Z-axis direction) will be used to make a description. That is, in a case where the lead-out direction of the treatment tool (not shown) by the elevator 36 when the distal end portion 30 is viewed from the proximal operation part 22 is set as an upward direction, the upward direction indicates a Z(+) direction and a downward direction which is a direction opposite to the upward direction indicates a Z(−) direction. Further, in this case, a right direction indicates an X(+) direction and a left direction indicates an X(−) direction. Furthermore, in this case, a forward direction (a direction toward the distal end in the major axis direction Ax of the insertion part 24) indicates a Y(+) direction and a rearward direction (a direction toward the proximal end in the major axis direction Ax of the insertion part 24) indicates a Y(−) direction. The Y-axis direction including the Y(+) direction and the Y(−) direction is a direction parallel to the major axis direction Ax of the insertion part 24. The Z-axis direction is a direction orthogonal to the major axis direction Ax. The X-axis direction is a direction orthogonal to each of the Y-axis direction and the Z-axis direction.

As shown in FIG. 1, the proximal operation part 22 is formed in a substantially cylindrical shape as a whole. The proximal operation part 22 has an operation-part body 46 provided with the elevating operation lever 20 and a grip portion 48 linked to the operation-part body 46. The grip portion 48 is a portion that is gripped by the operator when the endoscope 10 is operated, and the proximal end of the insertion part 24 is connected to the distal end side of the grip portion 48 through a bending-proof pipe 50. A link member 120 is disposed outside the operation-part body 46. The link member 120 moves in conjunction with the operation of the elevating operation lever 20. A wire fixing member 80 is housed and fixed on the proximal end side of the link member 120. The wire fixing member 80 fixes the wire 38 (not shown). The wire fixing member 80 fixes the wire 38 and the link member 120. That is, the elevating operation lever 20 and the wire 38 are mechanically connected to each other through the wire fixing member 80. The wire fixing member 80 may comprise, for example, a collet. The collet has a plurality of gaps. The collet closes the gaps to grip and fix the wire 38. The collet opens the gaps to release the fixing of the wire 38. The opening and closing of the gaps of the collet may be linked to, for example, the rotational operation of the wire fixing member 80.

The proximal end of a universal cable 52 is connected to the operation-part body 46, and a connector device 54 is provided in the distal end of the universal cable 52. The connector device 54 is connected to an endoscope processor apparatus 14. The endoscope processor apparatus 14 comprises a light source device 15 and an image processing device 16. The light source device 15 is provided with a processor-side connector 15A to which the connector device 54 is connected. Further, the display 18 that displays an image which is subjected to image processing by the image processing device 16 is connected to the image processing device 16. The endoscope system 12 has a configuration in which power, optical signals, and the like are transmitted between the endoscope 10 and the endoscope processor apparatus 14 in a non-contact manner through a connector portion that is constituted of the connector device 54 and the processor-side connector 15A. Accordingly, the light from the light source device 15 is transmitted through an optical fiber cable (not shown) and is emitted from the illumination window 74 (see FIG. 2) provided on the front end face of the distal end portion 30. Further, the optical signal of the image captured from the observation window 76 (see FIG. 2) is subjected to image processing by the image processing device 16 and is displayed as an image on the display 18.

Further, an air/water supply button 57 and a suction button 59 are arranged side by side on the operation-part body 46. The air/water supply button 57 is a button that can be operated in two stages, and air may be supplied to the air/water supply nozzle 58 (see FIG. 2) through the air/water supply tube 42 by the first-stage operation, and water may be supplied to the air/water supply nozzle 58 through the air/water supply tube 42 by the second-stage operation. Further, in a case where the suction button 59 is operated, body fluid, such as blood, may be sucked from the treatment tool outlet port 60 (see FIG. 3) through the treatment tool channel 37.

As shown in FIG. 1, a pair of angle knobs 62 and 62 that are used to perform operation for bending the bendable portion 28 are arranged on the operation-part body 46. The pair of angle knobs 62 and 62 are coaxially provided so as to be rotationally movable. For example, four angle wires (not shown) are connected to the angle knobs 62 and 62, and the bendable portion 28, and the angle wires are pushed and pulled by the rotationally moving operation of the angle knobs 62 and 62, so that the bendable portion 28 is vertically and laterally bent.

Further, the elevating operation lever 20 is rotatably provided coaxially with the angle knobs 62 and 62. The elevating operation lever 20 is rotationally operated by the hand of the operator who grips the grip portion 48. In a case where the elevating operation lever 20 is rotationally operated, the link member 120 moves, and the wire fixing member 80 fixed to the link member 120 moves. Since the wire 38 shown in FIG. 2 is fixed to the wire fixing member 80, the wire 38 is pushed and pulled by this operation. The wire 38 is operated to be pushed and pulled, whereby the posture of the elevator 36 connected to the distal end of the wire 38 is changed between the lying position and the elevating position.

As shown in FIG. 1, the grip portion 48 of the proximal operation part 22 comprises a treatment tool inlet port 64 into which the treatment tool is introduced. The treatment tool (not shown) of which the distal end as a leading end is introduced from the treatment tool inlet port 64 is inserted through the treatment tool channel 37 (see FIG. 3) and is led out of the treatment tool outlet port 60 (see FIG. 3). Examples of the treatment tool may include treatment tools such as biopsy forceps of which the distal end has a cup capable of collecting body tissue, a knife for endoscopic sphincterotomy (EST), or a contrast tube.

Next, the structure of the distal end portion 30 will be described with reference to FIGS. 2 and 3. FIG. 2 is a perspective view of the distal end portion, and FIG. 3 is an exploded perspective view of the distal end portion.

Figure 3:
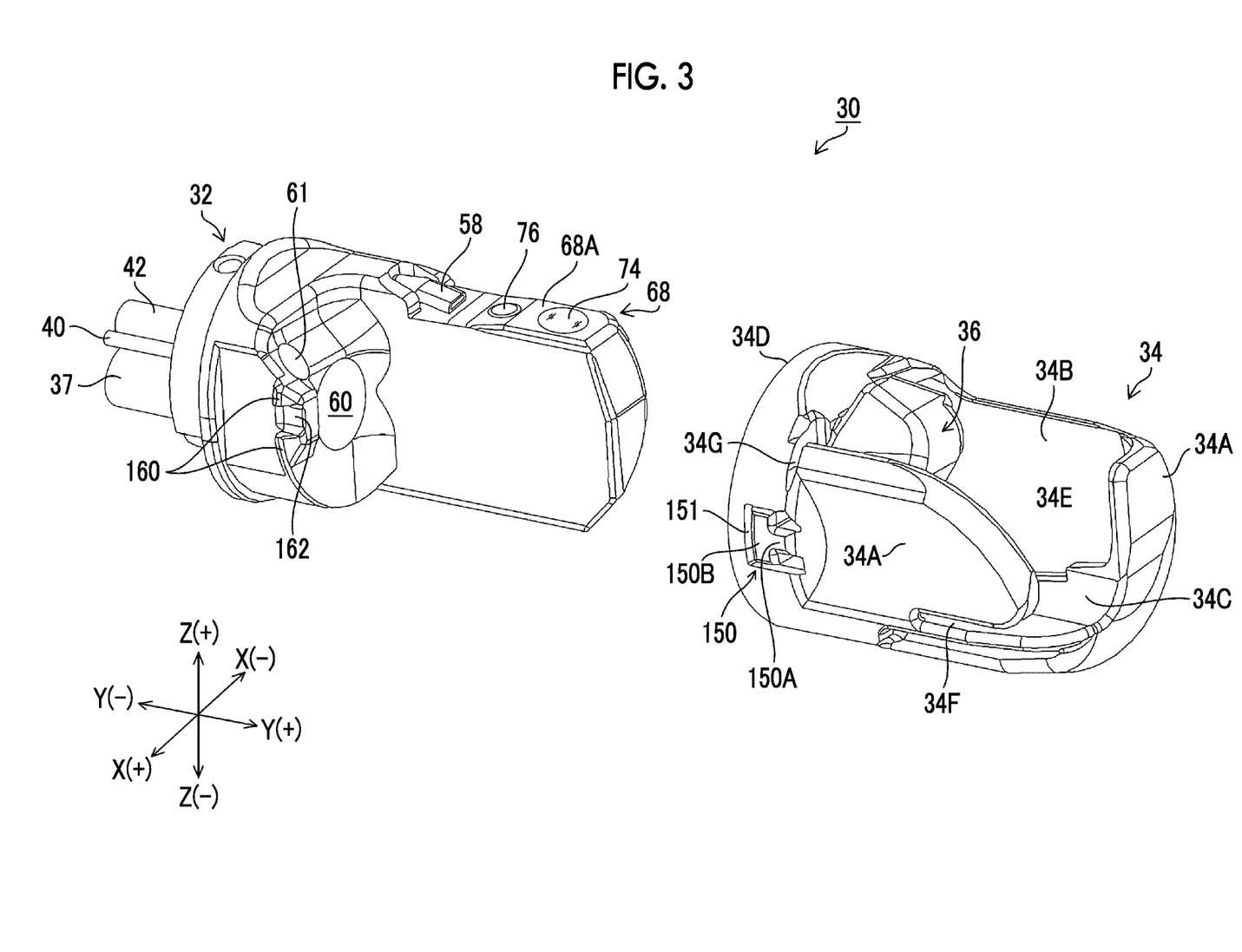
FIG. 3 is an exploded perspective view of the distal end portion.

The distal-end-portion body 32 is made of, for example, a metal material having corrosion resistance, and has a partition wall 68 provided in a protruding manner in the Y(+) direction as shown in FIGS. 2 and 3.

The illumination window 74 and an observation window 76 are arranged adjacent to each other in the Y-axis direction on the upper surface 68A on the Z(+) side of the partition wall 68. The illumination window 74 can irradiate the visual field region in the Z(+) direction with illumination light, and the observation window 76 can observe the visual field region in the Z(+) direction. The distal-end-portion body 32 is provided with the air/water supply nozzle 58 facing the observation window 76, and the observation window 76 is washed by air and water ejected from the air/water supply nozzle 58.

The distal end cap 34 shown in FIG. 2 or 3 is made of an elastic material, for example, a rubber material, such as fluororubber or silicone rubber, and a resin material, such as polysulfone or polycarbonate.

The distal end cap 34 comprises a cap opening 34B and a wall 34A that defines a distal end opening 34C continuous with the cap opening 34B. The wall 34A has a mounting opening 34D, and the mounting opening 34D allows the distal-end-portion body 32 to be inserted.

The distal end cap 34 is formed in a substantially tubular shape by the wall 34A that defines the cap opening 34B, the distal end opening 34C, and the mounting opening 34D, and an inner space 34E is formed in the distal end cap 34.

A through-hole 61 is formed in the distal-end-portion body 32, and the wire 38 (not shown) is inserted through the through-hole 61. The distal end of the wire 38 is connected to the elevator 36.

As shown in FIG. 2, when the distal end cap 34 is mounted on the distal-end-portion body 32, a part of the inner space 34E is occupied by the partition wall 68. The elevator housing space 66 is defined by the partition wall 68 and the wall 34A of the distal end cap 34. The elevator housing space 66 is disposed at a position on the X(+) direction side of the partition wall 68 and a position on the Y(+) direction side of the treatment tool outlet port 60.

As shown in FIG. 2, when the distal end cap 34 is mounted on the distal-end-portion body 32, the cap opening 34B is directed in the Z(+) direction. The treatment tool outlet port 60 (see FIG. 3) of the distal-end-portion body 32 communicates with the cap opening 34B through the elevator housing space 66.

The elevator 36 is rotatably supported in the inner space 34E of the distal end cap 34. A rotating shaft (not shown) is attached to the elevator 36. The rotating shaft is attached to the elevator 36 on the side opposite to the position facing the cap opening 34B. A bearing (not shown) that rotatably supports the rotating shaft of the elevator 36 is disposed in the inner space 34E of the distal end cap 34.

When the wire 38 shown in FIG. 2 is pushed and pulled, the elevator 36 is rotated about the rotating shaft, and the posture thereof is changed between the lying position and the elevating position.

The distal end cap 34 has a configuration in which the elevator 36 to which the wire 38 is connected is attached in advance. When the treatment using the endoscope 10 ends, the distal end cap 34 formed in this way is detached from the distal-end-portion body 32 as will be described later, and is discarded together with the elevator 36 and the wire 38 as, for example, a disposable member. The elevator 36 may be attached to the distal-end-portion body 32 instead of the distal end cap 34.

Next, mounting the distal end cap 34 on the distal-end-portion body 32 will be described with reference to FIGS. 3 to 5.

As shown in FIG. 3, the wall 34A of the distal end cap 34 faces the X(+) direction and the X(−) direction with the cap opening 34B interposed therebetween. The cantilever piece 150 is formed on the wall 34A opposite to the side where the partition wall 68 is inserted. A cutout 151 is provided in the distal end cap 34, whereby the cantilever piece 150 is formed. The cutout 151 penetrates the outside and the inside of the distal end cap 34.

The cantilever piece 150 comprises a support piece 150A and a stopped portion 150B connected to the support piece 150A. The side of the support piece 150A opposite to the stopped portion 150B is connected to the wall 34A to form a fixed end of the cantilever piece 150. The stopped portion 150B of the cantilever piece 150 is a free end that is not connected to the wall 34A. The cantilever piece 150 extends along the Y-axis direction, and the fixed end is positioned on the distal end side (Y(+) direction) than the free end.

The stopped portion 150B is larger in width in the Z-axis direction than the support piece 150A. When viewed in the X(+) direction, the cantilever piece 150 has a T-shape as a whole.

Since the support piece 150A is bent and deformed with the fixed end as a fulcrum, the stopped portion 150B, which is a free end, can be displaced in the X(+) direction and the X(−) direction.

As shown in FIG. 3, a first cut 34F and a second cut 34G are formed in the distal end cap 34. The first cut 34F is continuous with the distal end opening 34C and extends in the direction along the Y-axis direction. The first cut 34F penetrates the outside and the inside of the wall 34A of the distal end cap 34. The distal end cap 34 is divided into the Z(+) side and the Z(−) side with the first cut 34F as a boundary. The first cut 34F may not be completely parallel to the Y-axis direction as long as the first cut 34F extends along the Y-axis direction.

The second cut 34G extends in a direction orthogonal to the first cut 34F. The second cut 34G penetrates the outside and the inside of the wall 34A of the distal end cap 34. The second cut 34G is continuous with the cutout 151, extends in the Z(+) direction, and reaches the cap opening 34B. The distal end cap 34 is divided into the Y(+) side and the Y(−) side with the second cut 34G as a boundary. The first cut 34F and the second cut 34G have a positional relationship in which the first cut 34F and the second cut 34G are orthogonal to each other. Being orthogonal includes being completely orthogonal and being substantially orthogonal.

As shown in FIG. 3, the distal-end-portion body 32 has two stopper portions 160 on the side facing the cantilever piece 150. The two stopper portions 160 protrude in the X(+) direction. Further, the two stopper portions 160 are arranged along the Z-axis direction. A groove portion 162 is defined by the two stopper portions 160. The two stopper portions 160 are arranged at an interval that is narrower than the width of the stopped portion 150B and wider than the width of the support piece 150A.

Figure 4A:
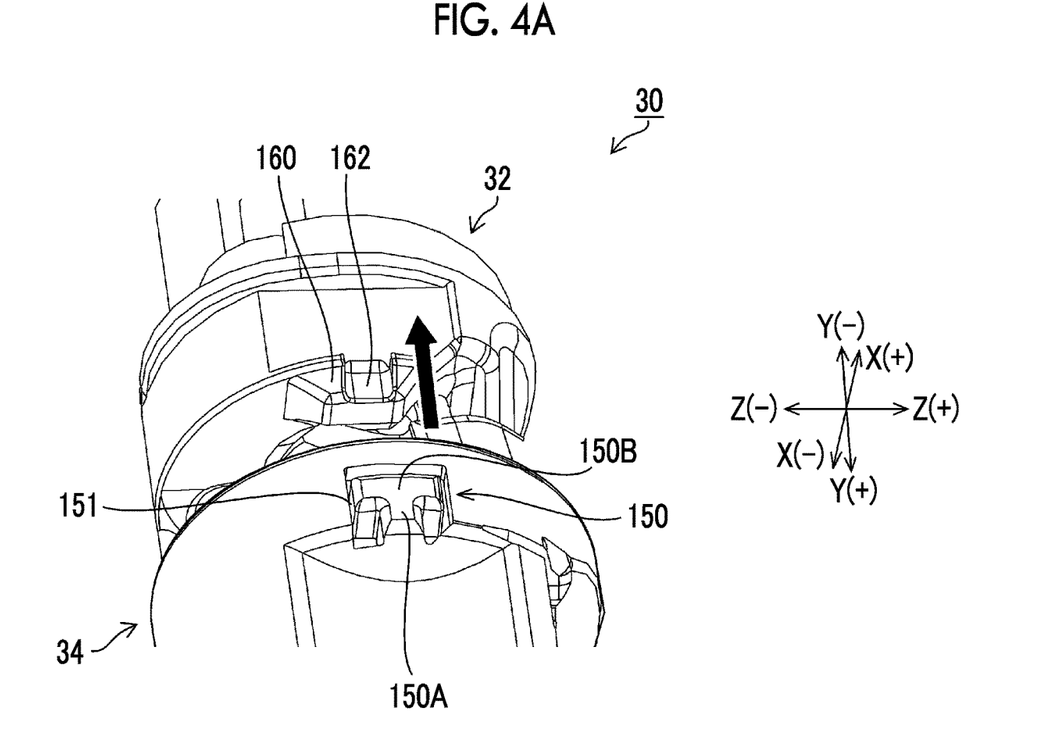
FIGS. 4A and 4B are enlarged perspective views of the distal end portion.
Figure 4B:
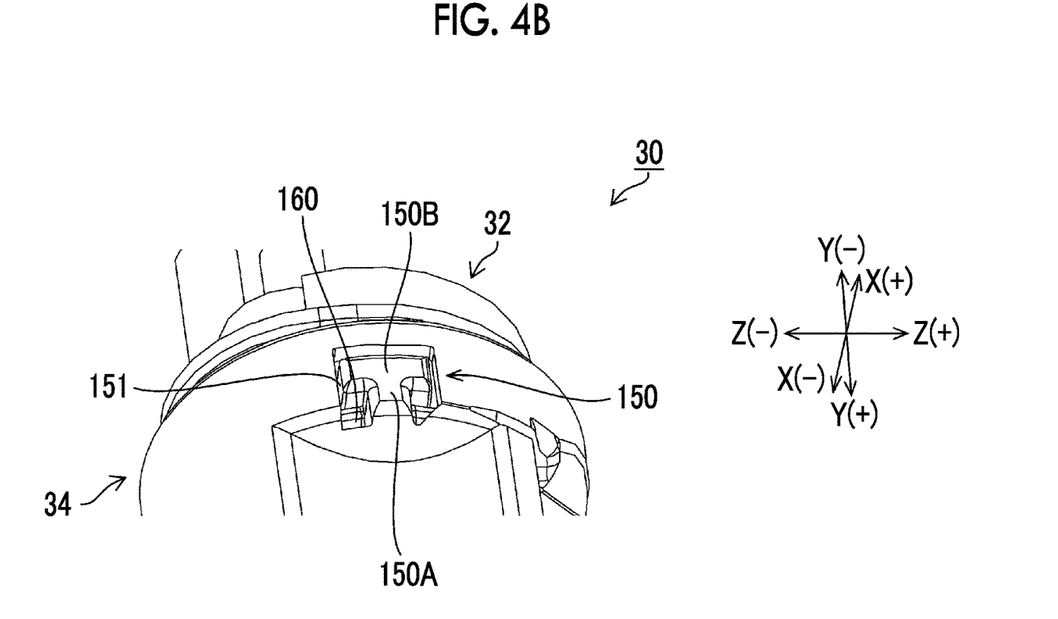

FIGS. 4A and 4B are enlarged perspective views of the distal end portion 30, and FIG. 4A shows a state immediately before the distal end cap 34 is mounted on the distal-end-portion body 32 and FIG. 4B shows a state after the distal end cap 34 is mounted on the distal-end-portion body 32. When the distal end cap 34 is mounted on the distal-end-portion body 32, the distal end cap 34 moves toward the distal-end-portion body 32 as shown in FIG. 4A.

As the distal end cap 34 moves, the stopped portion 150B of the cantilever piece 150 comes into contact with the two stopper portions 160. Further, when the distal end cap 34 moves toward the distal-end-portion body 32, the support piece 150A is bent and deformed in the X(+) direction with the fixed end as a fulcrum. The stopped portion 150B, which is a free end, moves in a direction of running on the two stopper portions 160.

As shown in FIG. 4B, when the distal end cap 34 moves to the mounting position with respect to the distal-end-portion body 32, the stopped portion 150B goes over the two stopper portions 160 and moves to the proximal end side (Y(−)) than the two stopper portions 160. The support piece 150A returns to the original state due to elastic deformation. As shown in FIG. 4A, since the interval between the two stopper portions 160 is narrower than the width of the stopped portion 150B, the two stopper portions 160 and the stopped portion 150B are engaged with each other. On the other hand, the support piece 150A is housed in the groove portion 162. The engagement between the stopper portions 160 and the stopped portion 150B prevents the distal end cap 34 from moving from the distal-end-portion body 32 in the Y(+) direction and falling out.

Figure 5:
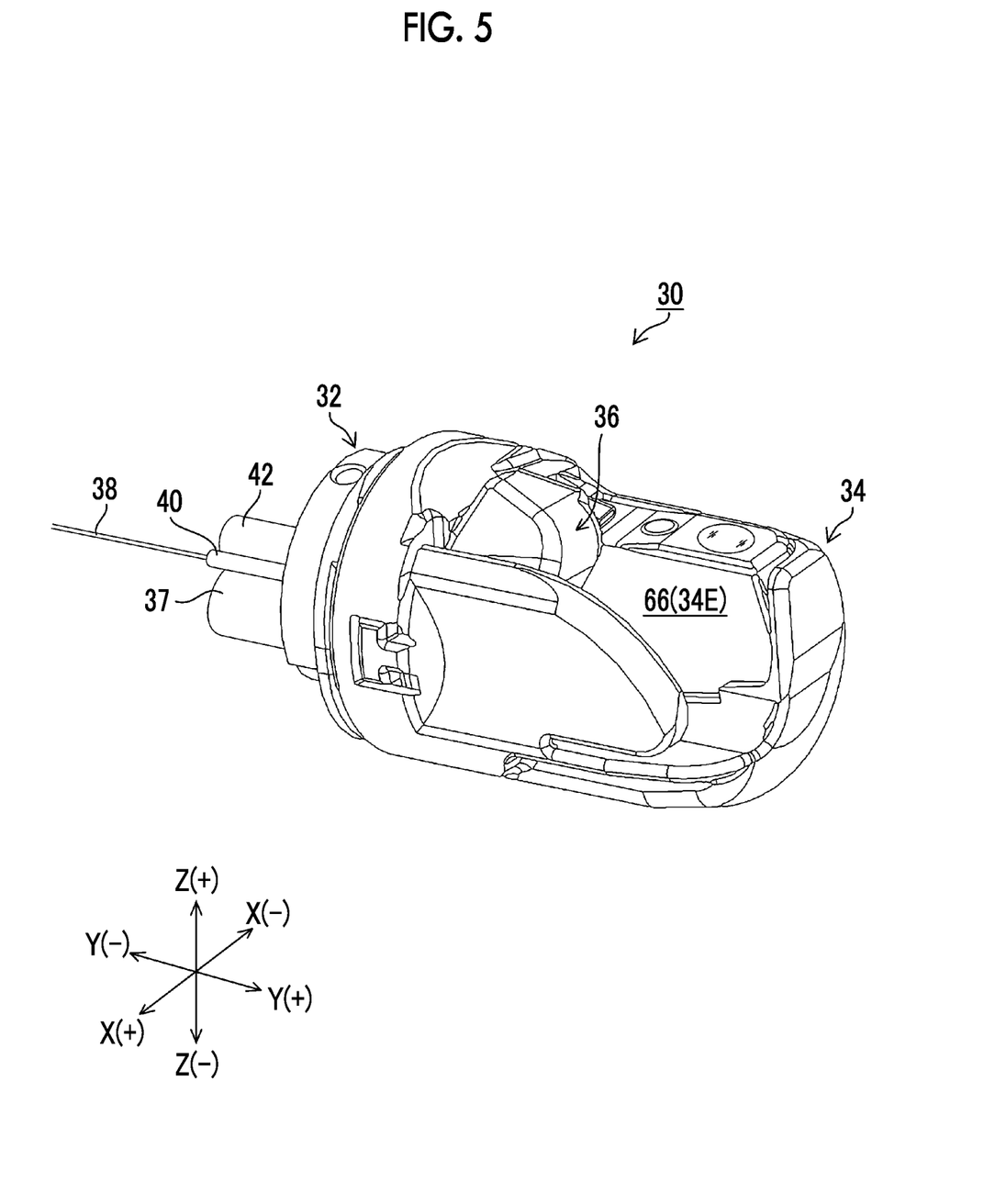
FIG. 5 is a perspective view of the distal end portion when viewed from an angle different from that of FIG. 2.

As shown in FIG. 5, the distal end cap 34 is mounted on the distal-end-portion body 32. In this state, the distal end portion 30 of the endoscope 10 is inserted into the object to be examined. The treatment tool is directed in a desired lead-out direction in the object to be examined by the elevator 36 of the distal end portion 30. After the treatment, the distal end cap 34 is detached and the distal end portion 30 is washed. Accordingly, it is required that the distal end cap 34 can be easily detached from the distal-end-portion body 32 and the damage or load applied to the endoscope 10 is suppressed.

Hereinafter, the distal-end-cap detachment jig will be described with reference to FIGS. 6A to 11.

First Embodiment

Figure 6A:
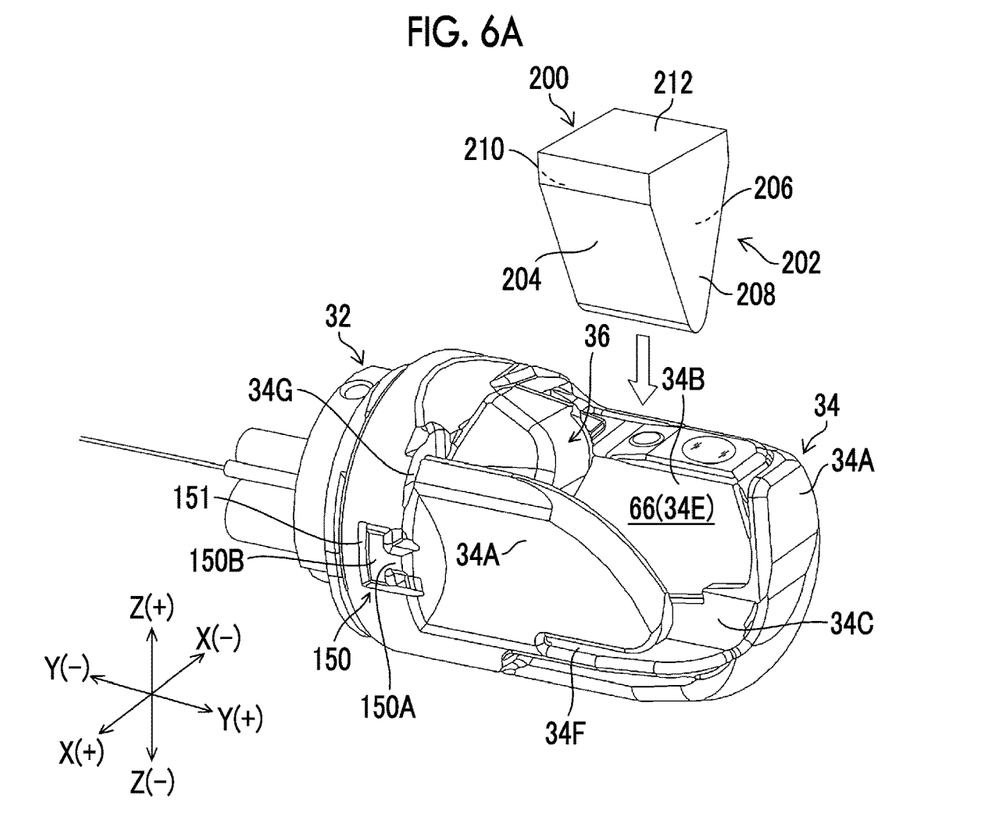
FIGS. 6A and 6B are perspective views showing a procedure for detaching the distal end cap using a first embodiment of a distal-end-cap detachment jig.
Figure 6B:
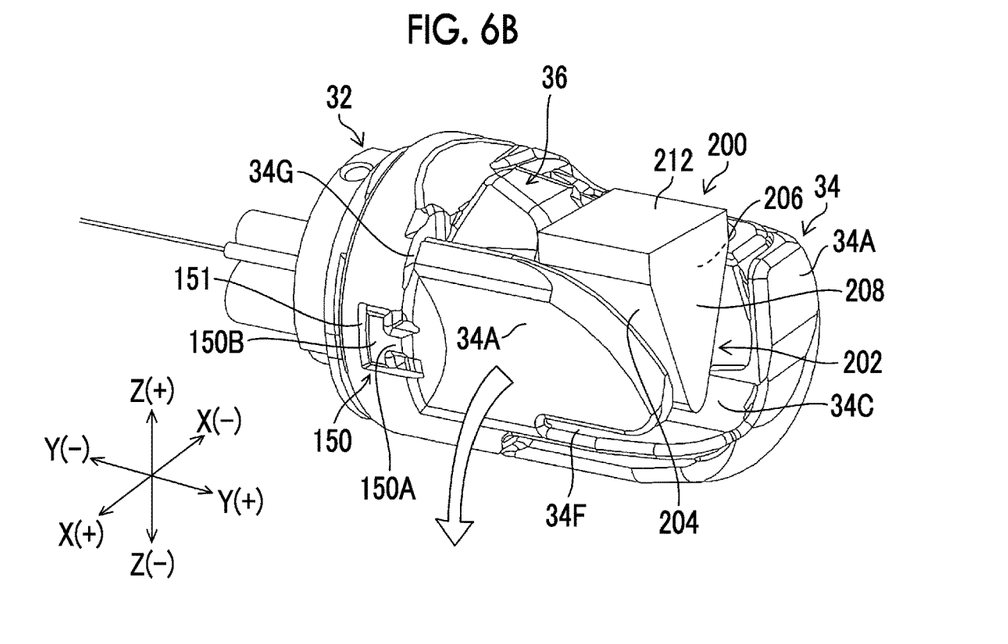

FIGS. 6A and 6B are perspective views showing a procedure for detaching the distal end cap using a first embodiment of the distal-end-cap detachment jig. FIG. 6A is a perspective view showing a state before a distal-end-cap detachment jig 200 is inserted into the distal end cap 34, and FIG. 6B is a perspective view showing a state after the distal-end-cap detachment jig 200 is inserted into the distal end cap 34.

As shown in FIG. 6A, the distal-end-cap detachment jig 200 comprises a body portion 202. The body portion 202 has two inclined surfaces 204 and 206 that face each other. The two inclined surfaces 204 and 206 are planes and are inclined with respect to the direction of insertion indicated by the arrow. The two inclined surfaces 204 and 206 intersect in the direction of insertion and form a tapered shape in the direction of insertion. The line of intersection between the inclined surfaces 204 and 206 extends in a straight line.

The body portion 202 comprises two planes 208 and 210 which face each other and connect the two inclined surfaces 204 and 206 to each other. The body portion 202 comprises a plane 212 parallel to the X-axis direction and the Y-axis direction, on the side opposite to the direction of insertion. It is preferable that the body portion 202 is integrally molded.

Since the body portion 202 of the distal-end-cap detachment jig 200 deforms the distal end cap 34, the body portion 202 is preferably made of a material harder than the distal end cap 34. For example, the body portion 202 is made of a resin material, a metal material, or the like.

As shown in FIG. 6A, the distal-end-cap detachment jig 200 is prepared. The position of the distal-end-cap detachment jig 200 is adjusted with respect to the distal end cap 34 in a direction in which the tapered part of the body portion 202 faces the cap opening 34B and at least one inclined surface 204 comes into contact with the wall 34A. The line of intersection between the two inclined surfaces 204 and 206 is positioned in a direction substantially parallel to the Y-axis direction. When the distal end cap 34 is mounted on the distal-end-portion body 32, the elevator housing space 66 and the inner space 34E of the distal end cap 34 substantially coincide with each other.

As shown in FIG. 6B, the body portion 202 is inserted into the inner space 34E of the distal end cap 34 through the cap opening 34B. For example, the plane 212 is pressed by a finger or the like, and the body portion 202 is pushed into the inner space 34E of the distal end cap 34.

The distance between the inclined surfaces 204 and 206 increases in a direction opposite to the direction of insertion. The distance between the inclined surfaces 204 and 206 at a certain position is larger than the distance between the partition wall 68 and the wall 34A positioned on the X(+) side with respect to the partition wall 68.

As the body portion 202 is inserted into the inner space 34E of the distal end cap 34, the inclined surface 204 pushes the wall 34A in the direction (X(+) direction) of expanding the inner space 34E of the distal end cap 34, to deform the distal end cap 34. The deformation of the distal end cap 34 facilitates the detachment of the distal end cap 34 from the distal-end-portion body 32. A load applied to the bendable portion 28 (not shown) can be suppressed.

In FIG. 6B, the deformation of the distal end cap 34 facilitates the release of the engaged stopped portion 150B and stopper portions 160.

In FIG. 6B, since the first cut 34F and the second cut 34G orthogonal to the first cut 34F are formed in the distal end cap 34, the wall 34A can be easily deformed.

The distal end cap 34 detached from the distal-end-portion body 32 is discarded without being reused.

Next, a first modification example of the first embodiment of a distal-end-cap detachment jig 300 will be described with reference to FIG. 7. The distal-end-cap detachment jig 300 comprises a connection portion 230 connected to the body portion 202. The connection portion 230 is connected to a plane 212 at a position opposite to the direction of insertion of the body portion 202. The connection portion 230 has an outer form 230A having a substantially semi-cylindrical shape and has a finger hole 230C penetrating two bottom surfaces 230B that face each other. The finger hole 230C extends in a direction orthogonal to the direction of insertion indicated by the arrow, and in FIG. 7, a direction along the line of intersection between the inclined surfaces 204 and 206.

In the first modification example, the operator handles the distal-end-cap detachment jig 300 in a state in which a finger is inserted into the finger hole 230C of the connection portion 230. The operator can easily insert the body portion 202 into the inner space 34E (see FIG. 6) of the distal end cap 34.

In the distal-end-cap detachment jig 300, the connection of the body portion 202 and the connection portion 230 includes a case where the body portion 202 and the connection portion 230 are integrally molded and a case where the body portion 202 and the connection portion 230 are formed as separate members and are bonded to each other using an adhesive or the like.

Figure 7:
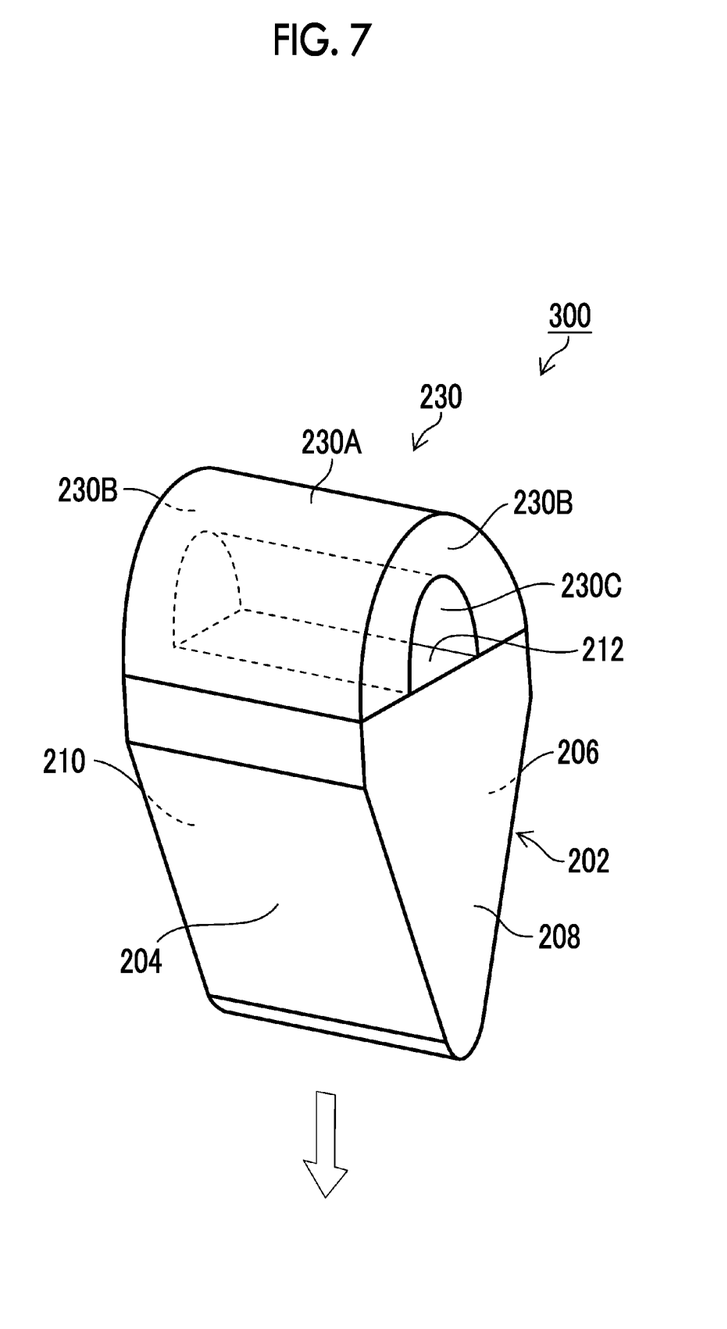
FIG. 7 is a perspective view showing a first modification example of the first embodiment of the distal-end-cap detachment jig.

The case where the finger hole 230C penetrates is illustrated in FIG. 7, but the finger hole 230C does not need to penetrate as long as the finger can be inserted.

Next, a second modification example of the first embodiment of a distal-end-cap detachment jig 400 will be described with reference to FIG. 8. The distal-end-cap detachment jig 400 comprises a connection portion 250 connected to the body portion 202.

The connection portion 250 comprises a fixed arm 252, a sliding arm 254, and a fulcrum portion 256 that connects one end of the fixed arm 252 to one end of the sliding arm 254. The body portion 202 is connected to the end part of the sliding arm 254 on the side opposite to the fulcrum portion 256. The direction of insertion of the body portion 202 is directed to the fixed arm 252 side.

A supporting surface 258 that is used to support the distal-end-portion body 32 on which the distal end cap 34 is mounted is provided on the side of the fixed arm 252 opposite to the fulcrum portion 256. The supporting surface 258 is preferably a curved surface that follows the shape of the distal end cap 34. The supporting surface 258 can stably support the distal-end-portion body 32 on which the distal end cap 34 is mounted.

The distal end cap 34 is detached by, for example, the following procedure. The distal-end-portion body 32 on which the distal end cap 34 is mounted is placed on the supporting surface 258 of the fixed arm 252 so that the distal end side faces the fulcrum portion 256. The operator applies a force to the sliding arm 254 toward the fixed arm 252. The body portion 202 is inserted into the inner space 34E of the distal end cap 34 (not shown), and as in the first embodiment, the inclined surface 204 pushes the wall 34A in the direction of expanding the inner space 34E of the distal end cap 34, to deform the distal end cap 34.

Figure 8:
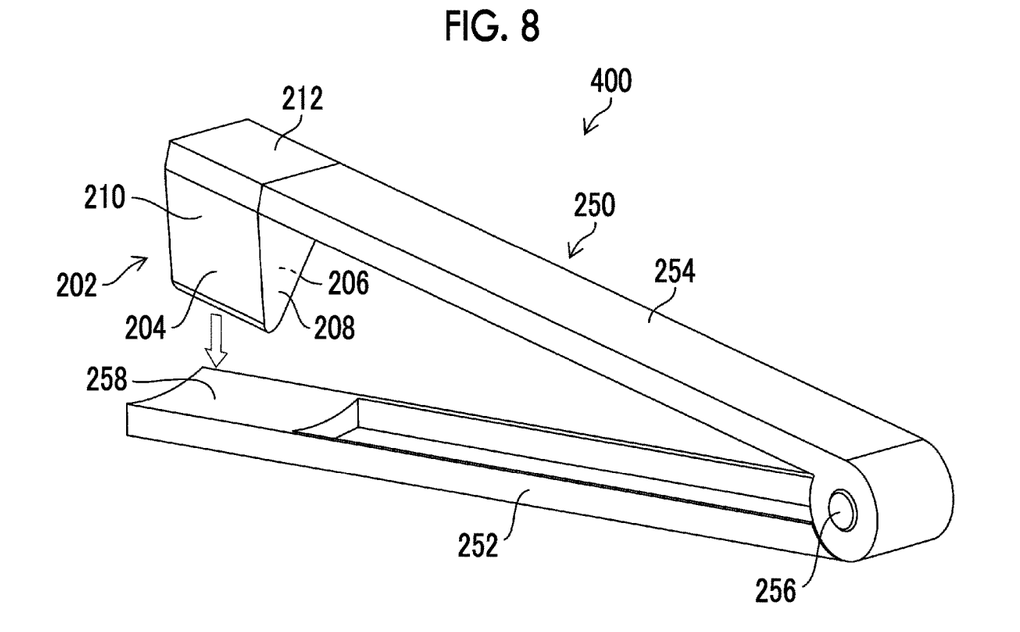
FIG. 8 is a perspective view showing a second modification example of the first embodiment of the distal-end-cap detachment jig.

The fulcrum portion 256 in FIG. 8 is formed of respective through-holes provided at one end of the fixed arm 252 and one end of the sliding arm 254 and a pin inserted into both the through-holes at the same time. In the fulcrum portion 256, it is preferable that a biasing force is applied by a spring element (not shown) in a direction in which the fixed arm 252 and the sliding arm 254 are spaced apart from each other.

The fixed arm 252, the sliding arm 254, and the fulcrum portion 256 may be integrally molded. For example, a strip-shaped metal member is bent at substantially the center thereof, whereby the connection portion 250 may be formed. The bent portion forms the fulcrum portion.

Second Embodiment

Figure 9:
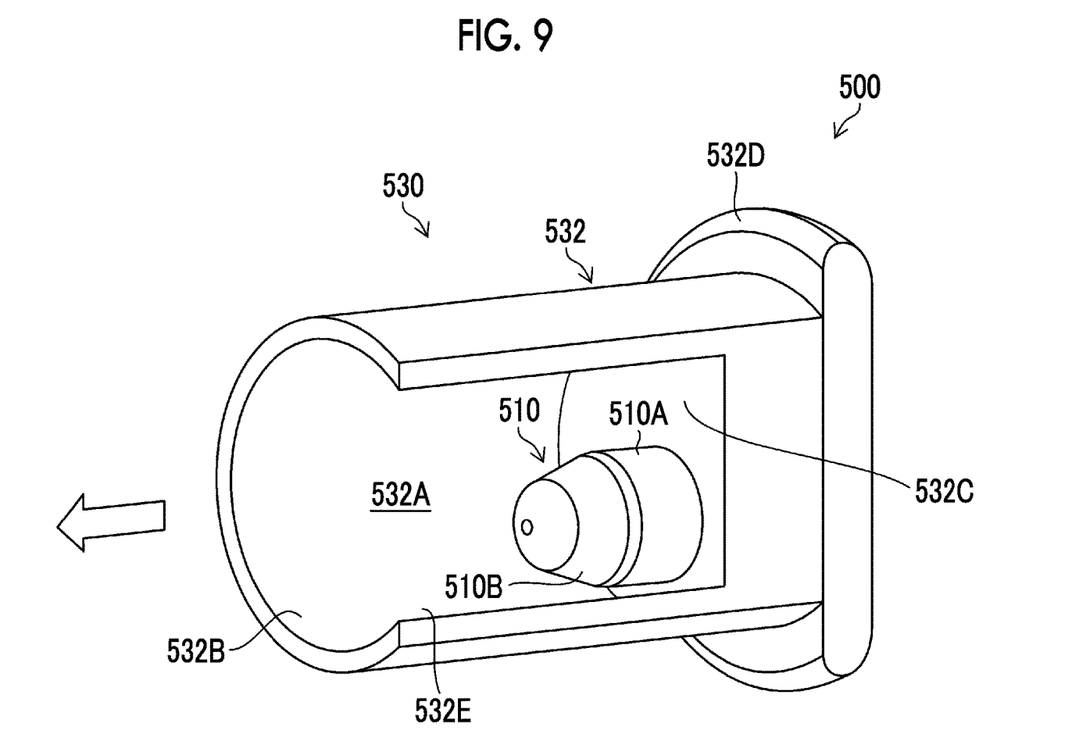
FIG. 9 is a perspective view of a second embodiment of the distal-end-cap detachment jig.

FIG. 9 is a perspective view showing a second embodiment of the distal-end-cap detachment jig. A distal-end-cap detachment jig 500 comprises a body portion 510 and a connection portion 530 connected to the body portion 510.

The body portion 510 has a shape different from the body portion 202 of the first embodiment. The body portion 510 comprises a cylindrical part 510A and a distal end part 510B that is continuous with the cylindrical part 510A and that becomes tapered as the distal end part 510B becomes farther from the cylindrical part 510A. The distal end part 510B has a substantially conical shape, and the side surface thereof forms an inclined surface that is tapered in the direction of insertion indicated by the arrow. The distal end shape of the distal end part 510B may be a dome shape formed by a curved surface as shown in FIG. 9, a flat surface, or a needle shape that converges to one point as long as the distal end part 510B comprises the inclined surface that is tapered in the direction of insertion.

The connection portion 530 comprises a housing member 532 in which a space 532A housing the distal end cap 34 is formed. The housing member 532 has a first opening 532B that allows housing the distal end cap 34, and a bottom 532C that faces the first opening 532B.

The body portion 510 is connected to the bottom 532C of the housing member 532 at a position opposite to the direction of insertion of the body portion 510. The housing member 532 comprises a flange 532D on the side opposite to the first opening 532B.

The housing member 532 shown in FIG. 9 comprises preferably a second opening 532E facing the side orthogonal to the direction of insertion of the body portion 510. Since the second opening 532E is formed, the housing member 532 has a substantially C-shaped gutter shape in a cross-section taken along a direction orthogonal to the direction of insertion.

In the distal-end-cap detachment jig 500, the connection of the body portion 510 and the connection portion 530 includes a case where the body portion 510 and the connection portion 530 are integrally molded and a case where the body portion 510 and the connection portion 530 are formed as separate members and are bonded to each other using an adhesive or the like.

The distal-end-cap detachment jig 500 may be made of the same material as in the first embodiment.

Figure 10A:
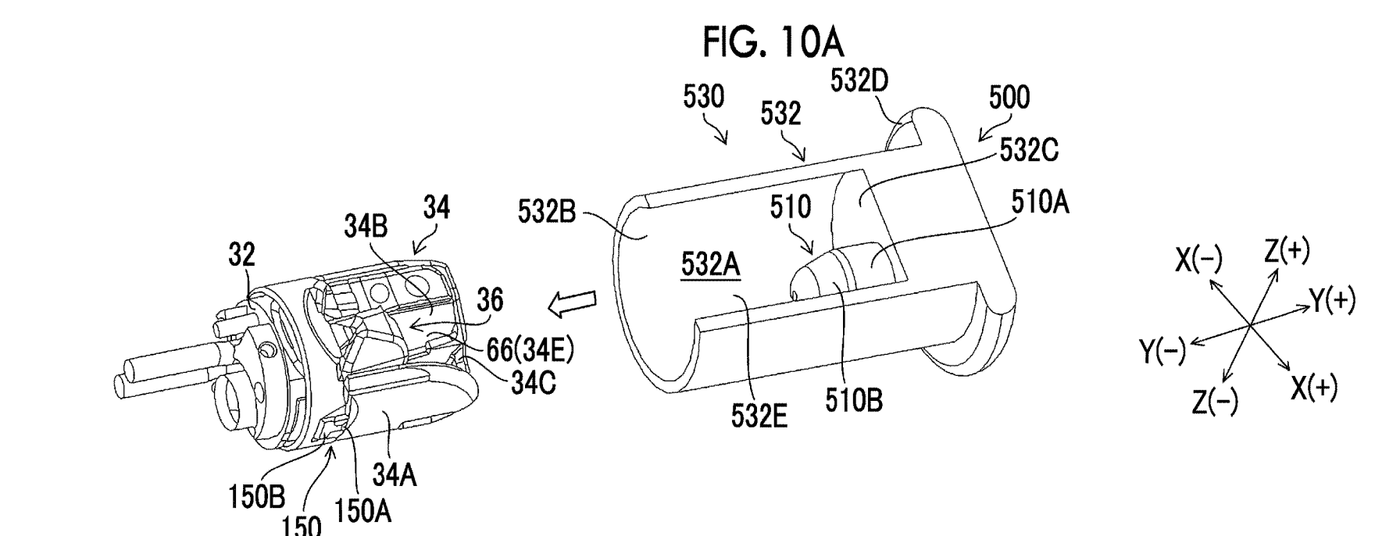
FIGS. 10A and 10B are perspective views showing a procedure for detaching the distal end cap using the second embodiment of the distal-end-cap detachment jig.
Figure 10B:
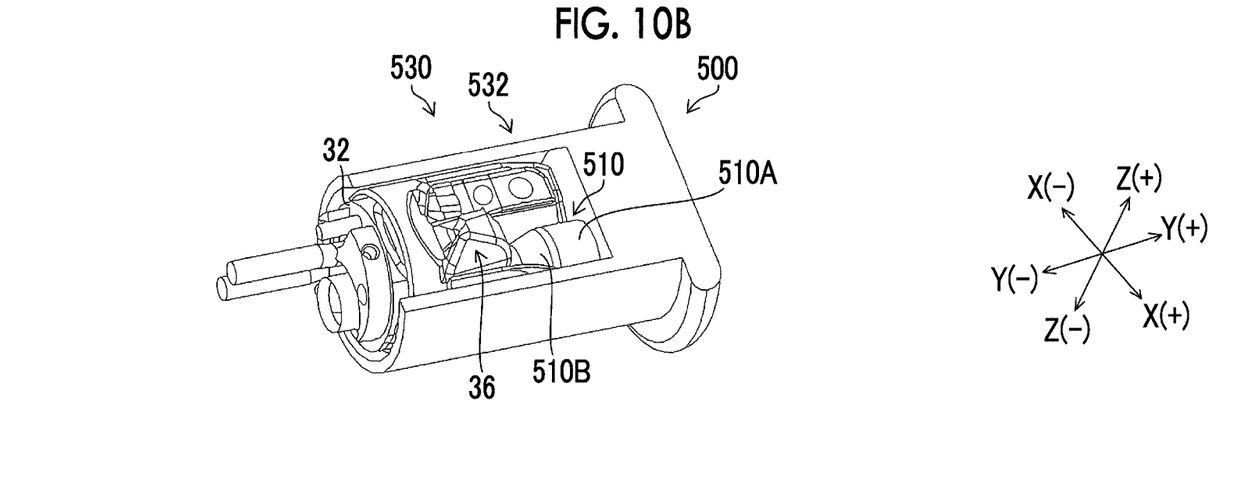

FIGS. 10A and 10B are perspective views showing a procedure for detaching the distal end cap using the second embodiment of the distal-end-cap detachment jig. FIG. 10A is a perspective view showing a state before the distal-end-cap detachment jig 500 is inserted into the distal end cap 34, and FIG. 10B is a perspective view showing a state after the distal-end-cap detachment jig 500 is inserted into the distal end cap 34.

As shown in FIG. 10A, the distal-end-cap detachment jig 500 is prepared. The position of the distal-end-cap detachment jig 500 is adjusted with respect to the distal end cap 34 in a direction in which the tapered part of the body portion 510 faces the distal end opening 34C and at least the inclined surface included in the distal end part 510B comes into contact with the wall 34A. The distal-end-cap detachment jig 500 is disposed in a state in which the first opening 532B of the housing member 532 faces the distal end cap 34 side and the second opening 532E of the housing member 532 faces the Z(+) side. As in the first embodiment, the elevator housing space 66 and the inner space 34E of the distal end cap 34 substantially coincide with each other.

As shown in FIG. 10B, the distal-end-portion body 32 on which the distal end cap 34 is mounted is housed in a space 532A of the housing member 532, and the body portion 510 is inserted into the inner space 34E of the distal end cap 34 through the distal end opening 34C. For example, the body portion 510 is pushed into the inner space 34E of the distal end cap 34 while the housing member 532 is held by a finger or the like.

The diameter of the inclined surface included in the distal end part 510B increases in the direction opposite to the direction of insertion. The outer diameter of the distal end part 510B formed by the inclined surface at a certain position is larger than the distance between the partition wall 68 and the wall 34A positioned on the X(+) side with respect to the partition wall 68.

As the body portion 510 is inserted into the inner space 34E of the distal end cap 34, the inclined surface of the distal end part 510B pushes the wall 34A in the direction (X(+) direction) of expanding the inner space 34E of the distal end cap 34, to deform the distal end cap 34. The deformation of the distal end cap 34 facilitates the detachment of the distal end cap 34 from the distal-end-portion body 32. Damage to the observation window 76 of the distal-end-portion body 32 can be suppressed.

In FIG. 10B, the operator can visually recognize the deformed state of the distal end cap 34 through the second opening 532E of the housing member 532.

Further, the deformation of the distal end cap 34 facilitates the release of the engaged stopped portion 150B and stopper portions 160.

Further, since the first cut 34F and the second cut 34G are formed in the distal end cap 34, the wall 34A can be easily deformed.

The distal end cap 34 detached from the distal-end-portion body 32 is discarded without being reused.

Figure 11:
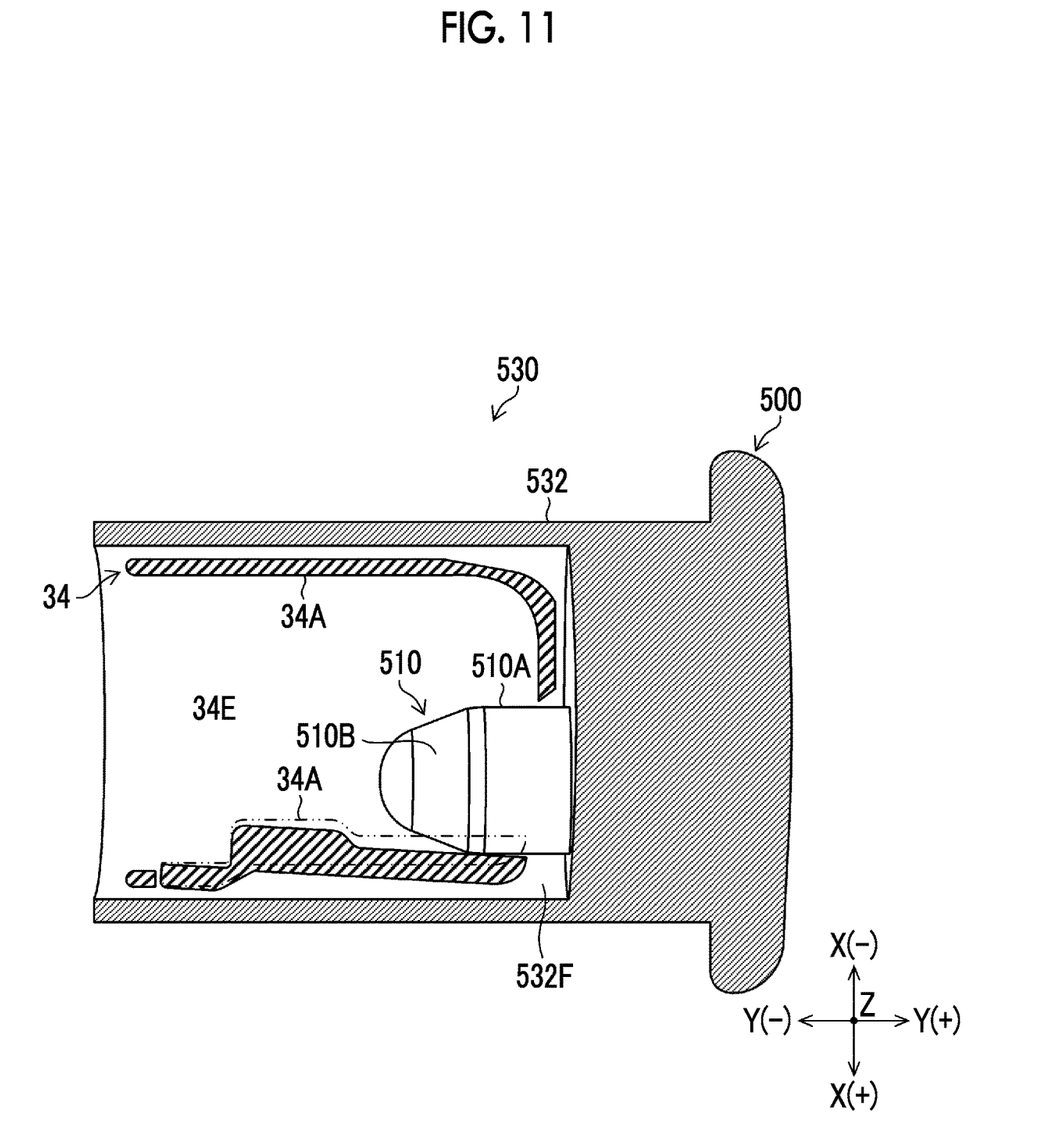
FIG. 11 is a cross-sectional view of the distal-end-cap detachment jig in a state in which the distal-end-cap detachment jig is inserted into the distal end cap.

FIG. 11 is a cross-sectional view that is taken along a plane parallel to the X-axis direction and the Y-axis direction and passing through the substantially center of the body portion 510, in the state of FIG. 10B. As shown in FIG. 11, when the body portion 510 is inserted into the inner space 34E of the distal end cap 34, the inclined surface of the distal end part 510B pushes the wall 34A in the X(+) direction to deform the distal end cap 34.

In order to make the distal end cap 34 deformable, the space 532A has a size in which the space 532A includes an escape space 532F between the wall 34A of the distal end cap 34 and the interior wall of the housing member 532.

In the first and second embodiments, the independent distal-end-cap detachment jig has been exemplified. However, the distal-end-cap detachment jig may be provided on a mounting part mounted on the operation part of the side-viewing scope. In this case, it is not necessary to wash and disinfect the distal-end-cap detachment jig itself. Further, the risk of losing the distal-end-cap detachment jig can be avoided.

EXPLANATION OF REFERENCES

10: endoscope
12: endoscope system
14: endoscope processor apparatus
15: light source device
15A: processor-side connector
16: image processing device
18: display
20: elevating operation lever
22: proximal operation part
24: insertion part
26: soft portion
28: bendable portion
30: distal end portion
32: distal-end-portion body
34: distal end cap
34A: wall
34B: cap opening
34C: distal end opening
34D: mounting opening
34E: inner space
34F: first cut
34G: second cut
36: treatment tool elevator
37: treatment tool channel
38: elevating operation wire
40: wire channel
42: air/water supply tube
44: cable insertion channel
46: operation-part body
48: grip portion
50: bending-proof pipe
52: universal cable
54: connector device
57: air/water supply button
58: air/water supply nozzle
59: suction button
60: treatment tool outlet port
61: through-hole
62: angle knob
64: treatment tool inlet port
66: elevator housing space
68: partition wall
68A: upper surface
74: illumination window
76: observation window
80: wire fixing member 120: link member
150: cantilever piece
150A: support piece
150B: stopped portion
160: stopper portion
162: groove portion
200: distal-end-cap detachment jig
202: body portion
204: inclined surface
206: inclined surface
208: plane
210: plane
212: plane
230: connection portion
230A: outer form
230B: bottom surface
230C: finger hole
250: connection portion
252: fixed arm
254: sliding arm
256: fulcrum portion
258: supporting surface
300: distal-end-cap detachment jig
400: distal-end-cap detachment jig
500: distal-end-cap detachment jig
510: body portion
510A: cylindrical part
510B: distal end part
530: connection portion
532: housing member
532A: space
532B: first opening
532C: bottom
532D: flange
532E: second opening
532F: space
Ax: major axis direction

What is claimed is:

1. A distal-end-cap detachment jig that is used to detach a distal end cap mounted on a distalend of a side-viewing scope, the distal end cap having an inner space which communicates with a cap opening allowing a passage of a treatment tool, the distal-end-cap detachment jig comprising:
   a tubular-shaped housing member in which a space that houses the distal end cap is formed;
   a first opening which is formed to the tubular-shaped housing member and through which the distal end cap is insertable;
   a bottom which is formed to the tubular-shaped housing member and faces the first opening; and
   a body portion which has a cylindrical shape and is configured to be insertable into the inner space, and of which one end in a longitudinal direction of the cylindrical shape is connected to the bottom of the tubular-shaped housing member in the space of the tubular-shaped housing member,
   wherein the other end in the longitudinal direction of the cylindrical shape of the body portion has a tapered shape which is tapered toward a distal end side in a direction of insertion into the inner space of the distal end cap,
   the body portion has a maximum width larger than a width of the inner space of the distal end cap, wherein the maximum width of the body portion and the width of the inner space is on a plane perpendicular to the direction of insertion, and
   wherein the body portion is configured to enter the cap opening, deform the distal end cap and expand the inner space in the distal end cap.

2. The distal-end-cap detachment jig according to claim 1, further comprising:
   a connection portion that is connected to the body portion,
   wherein the connection portion is connected at a position opposite to the direction of insertion of the body portion and is provided with a finger hole extending in a direction orthogonal to the direction of insertion.

3. The distal-end-cap detachment jig according to claim 2, wherein the finger hole is a through-hole that penetrates the connection portion.

4. The distal-end-cap detachment jig according to claim 1, further comprising:
   a connection portion that is connected to the body portion,
   wherein the connection portion includes a fixed arm, a sliding arm, and a fulcrum portion that connects one end of the fixed arm to one end of the sliding arm,
   the body portion is connected to an end part of the sliding arm on a side opposite to the fulcrum portion, and
   the body portion can be inserted into the inner space of the distal end cap with the fulcrum portion as a fulcrum.

5. The distal-end-cap detachment jig according to claim 4, wherein a side of the fixed arm opposite to the fulcrum portion is formed by a curved surface that follows a shape of the distal end cap.

6. The distal-end-cap detachment jig according to claim 1, wherein the space includes an escape space that houses the distal end cap deformed by the body portion.

7. The distal-end-cap detachment jig according to claim 1, wherein the tubular-shaped housing member has a second opening that is opened toward a side orthogonal to the direction of insertion of the body portion.

* * * * *